United States Patent
Furuya et al.

(10) Patent No.: US 6,572,602 B2
(45) Date of Patent: Jun. 3, 2003

(54) ABSORBENT ARTICLE WITH BACKING SHEET HAVING CONTINUOUS FILAMENTS

(75) Inventors: Kodai Furuya, Kagawa (JP); Hiroo Hayashi, Kagawa (JP); Takamitsu Igaue, Kagawa (JP); Shinya Kaneko, Kagawa (JP)

(73) Assignee: Uni-Charm Corporation, Kawanoe (JP)

( * ) Notice: Subject to any disclaimer, the term of this patent is extended or adjusted under 35 U.S.C. 154(b) by 0 days.

(21) Appl. No.: 09/940,146

(22) Filed: Aug. 22, 2001

(65) Prior Publication Data

US 2002/0029026 A1 Mar. 7, 2002

(30) Foreign Application Priority Data

Sep. 1, 2000 (JP) ........................................ 2000-265527

(51) Int. Cl.[7] ............................................. A61F 113/15
(52) U.S. Cl. .................... 604/391; 604/385.03; 604/387
(58) Field of Search .......................... 604/385.01, 358, 604/384, 385.03, 391, 387

(56) References Cited

U.S. PATENT DOCUMENTS

| | | | |
|---|---|---|---|
| 3,727,615 A | * 4/1973 | Duchane | 128/290 |
| RE31,825 E | * 2/1985 | Mason et al. | 428/198 |
| 4,869,724 A | * 9/1989 | Scripps | 604/389 |
| 5,032,122 A | 7/1991 | Noel et al. | 604/391 |
| 5,256,231 A | 10/1993 | Gorman et al. | 156/178 |
| 5,843,066 A | * 12/1998 | Dobrin | 604/385.1 |
| 5,928,212 A | * 7/1999 | Kline et al. | 604/391 |

FOREIGN PATENT DOCUMENTS

| | | | | |
|---|---|---|---|---|
| EP | 1 048 236 | 11/2000 | | A44B/18/00 |
| GB | 2 327 857 | 2/1999 | | A61F/13/62 |
| WO | WO 97/25893 | 7/1997 | | A44B/18/00 |
| WO | WO 99/14045 | 3/1999 | | B32B/27/12 |

OTHER PUBLICATIONS

European Search Report.

* cited by examiner

*Primary Examiner*—Weilun Lo
*Assistant Examiner*—Jacqueline Stephens
(74) *Attorney, Agent, or Firm*—Darby & Darby

(57) ABSTRACT

There is disclosed an absorbent article including: a liquid permeable surface sheet; a backing sheet; and an absorbent layer located between the surface sheet and the backing sheet. The backing sheet includes a liquid impermeable base sheet and a layer of continuous filaments individually extending along a longitudinal direction of the absorbent article and stacked on an outer surface of the base sheet. The base sheet and the continuous filament layer are partially fixed.

6 Claims, 5 Drawing Sheets

ABSORBENT ARTICLE WITH BACKING SHEET HAVING CONTINUOUS FILAMENTS

BACKGROUND OF THE INVENTION

1. Field of the Invention

The present invention relates to an absorbent article, such as disposable diaper, incontinence pad, in which a backing sheet is formed with continuous filaments.

2. Description of the Related Art

Absorbent article, such as disposable diaper, incontinence pad (urine-absorbing pad) and so forth is provided with a liquid permeable surface sheet on an inner surface of an absorbent layer and a liquid impermeable backing sheet on an outer surface.

The backing sheet is required a function for shutting off a liquid and is desired to have moisture permeability (air permeability) for reducing stuffy (frowst) feeling on a wearer. In the conventional disposable diaper, a moisture permeable (air permeable) film formed by forming fine air holes in a polyolefin type resin film, is used as the backing sheet.

However, the backing sheet formed of the resin film provides stiff contact feeling to the touch. Moreover, it degrades external appearance. In order to deal with this problem, there has been known a disposable diaper in which a non-woven fabric is provided to appear on the outer surface of the disposable diaper to thereby provide cloth-like contact feeling and external appearance.

For example, such a backing sheet employing a non-woven fabric is prepared by stacking a non-woven fabric on the outer surface of a liquid impermeable resin film and by fixing the resin film and the non-woven fabric substantially over the entire confronting faces or partially by hot melt type adhesive. In another method, it is prepared by extruding a molten resin onto one surface of a non-woven fabric for lamination to thereby integrate a resin film on the non-woven fabric.

However, the backing sheet in which the resin film and the non-woven fabric are adhesive bonded, becomes stiff as a whole, because fibers of the non-woven fabric are constrained as bonded with the resin film. This results in degradation of fit to the wearer's body and feeling to the touch. On the other hand, the backing sheet in which the molten resin is laminated on the non-woven fabric, becomes further stiff, because the entire surface of the non-woven fabric is constrained by the resin film.

In addition, since the non-woven fabric is manufactured by bonding staple fibers to lower freedom of movement of individual fibers, soft feeling on the surface is restricted to lower texture. Moreover, ends of the fibers inherently appear on the surface of the non-woven fabric to degrade feeling to the touch.

Furthermore, the backing sheet having the non-woven fabric on the resin film requires bonding process or lamination process in manufacturing, large scale manufacturing facility is required to cause high manufacturing cost.

SUMMARY OF THE INVENTION

The present invention has been worked out in view of the shortcoming in the prior art as set forth above. It is an object of the present invention to provide an absorbent article using a backing sheet easy to manufacture, with high bulkiness for soft feeling and with the outer surface providing good feeling to the touch.

According to the invention, there is disclosed an absorbent article comprising:

a liquid permeable surface sheet;

a backing sheet;

an absorbent layer located between the surface sheet and the backing sheet;

the backing sheet including a liquid impermeable base sheet and a layer of continuous filaments individually extending along a longitudinal direction of the absorbent article and stacked on an outer surface of the base sheet, and the base sheet and the continuous filament layer being partially fixed.

Preferably, the base sheet and the continuous filament layer are fixed with each other at a plurality of fixing lines extending in a direction traversing the continuous filaments and spaced apart in a direction along which the continuous filaments extend. In this case, for example, the fixing line is in wave shaped pattern.

According to the invention, since the outer surface of the backing sheet is formed of the continuous filaments, the backing sheet becomes so bulky as to provide satisfactory cushioning ability. Especially since the continuous filaments extend continuously in the backing sheet, no fiber end appears on the outer surface of the backing sheet. Therefore, the outer surface of the backing sheet becomes so smooth. These continuous filaments can be prevented from falling out of the base sheet merely by partially fixing (bonding) them to the base sheet at fixing lines or the like. Therefore, fixing area (bond area) for the continuous filaments can be minimized to make the overall backing sheet soft. In the case where the base sheet is moisture permeable (air permeable), moreover, the continuous filament layer does not inhibit moisture permeability.

The absorbent article may be constructed such that the absorbent article has an intermediate portion for confronting a crotch portion of a wearer, a front portion for confronting an abdominal portion of a wearer and a rear portion for confronting a hip portion of a wearer, and that the rear portion is provided on laterally opposite side portions thereof with fasteners having engaging projections for engaging with the continuous filament layer in the front portion. In this case, bulkiness of the continuous filament layer is preferably increased at a region to which the fastener is intended to be engaged.

Moreover, the continuous filaments may be colored.

BRIEF DESCRIPTION OF THE DRAWINGS

The present invention will be understood more fully from the detailed description given hereinafter and from the accompanying drawings of the preferred embodiment of the present invention, which, however, should not be taken to be limitative to the invention, but are for explanation and understanding only.

In the drawings.

DESCRIPTION OF THE PREFERRED EMBODIMENT

The present invention will be discussed hereinafter in detail in terms of the preferred embodiment of the present invention with reference to the accompanying drawings. In the following description, numerous specific details are set forth in order to provide a thorough understanding of the present invention. It will be obvious, however, to those skilled in the art that the present invention may be practiced without these specific details. In other instance, well-known structure are not shown in detail in order to avoid unnecessary obscurity of the present invention.

Figure 1:
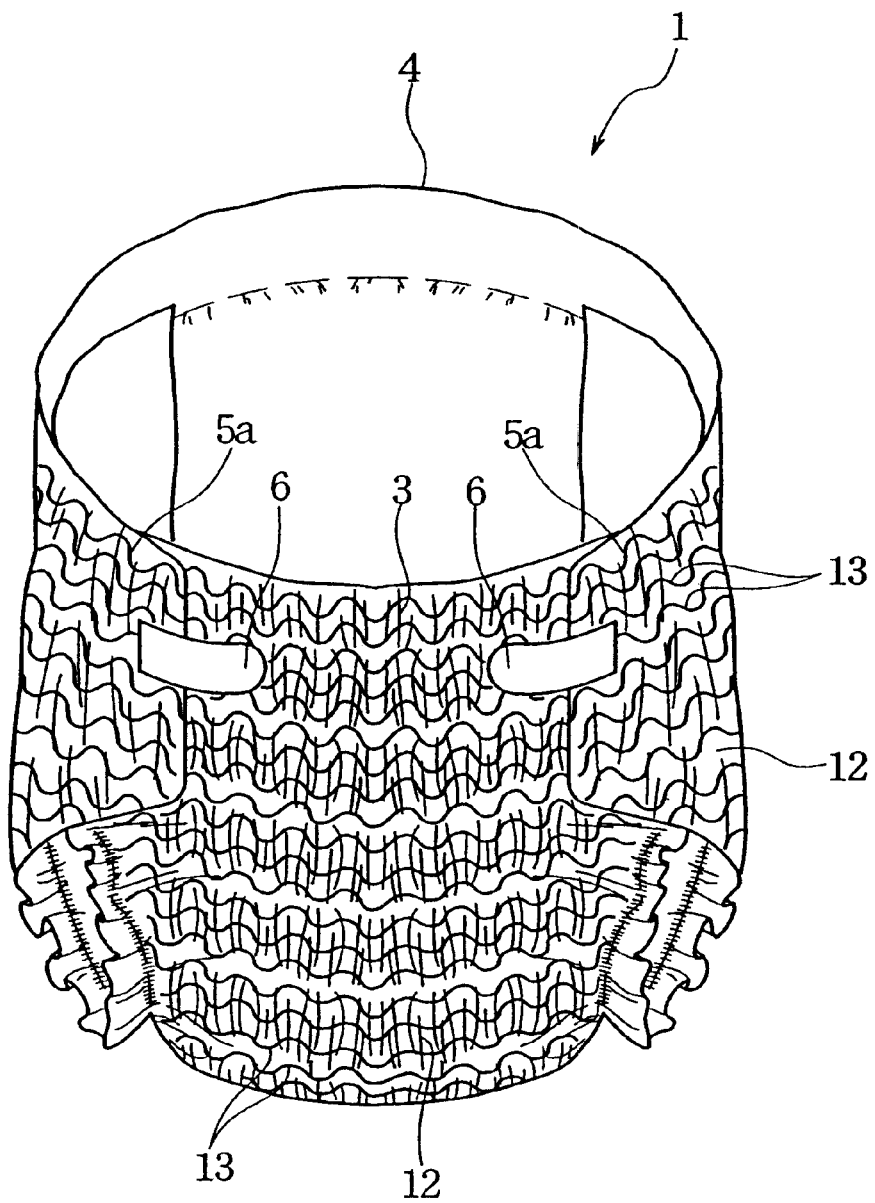
FIG. 1 is a perspective view showing a three-dimensional disposable diaper as an embodiment of an absorbent article according to the present invention.
Figure 2:
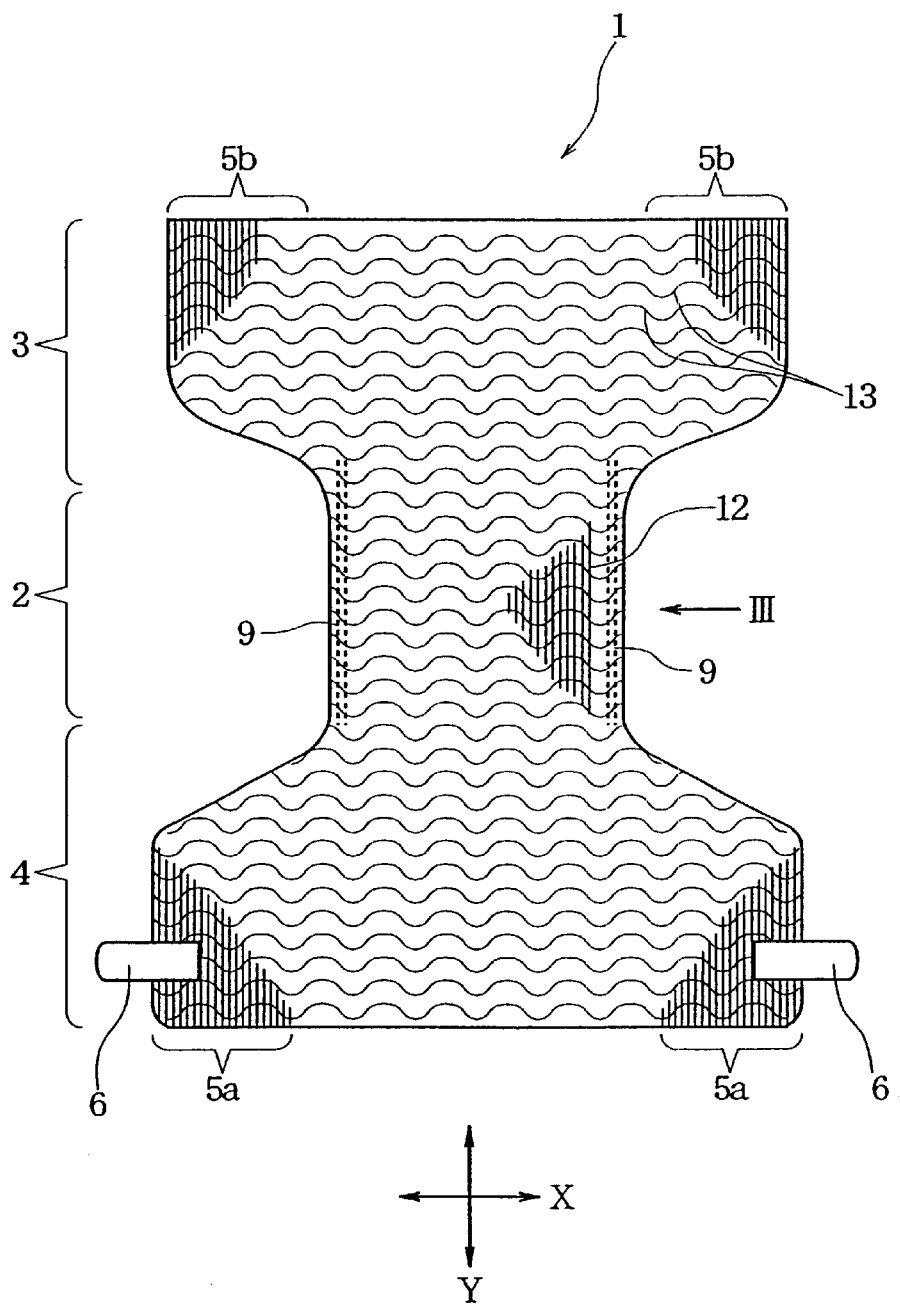
FIG. 2 is a developed plan view of the disposable diaper of FIG. 1 as viewed from outer surface.
Figure 3:
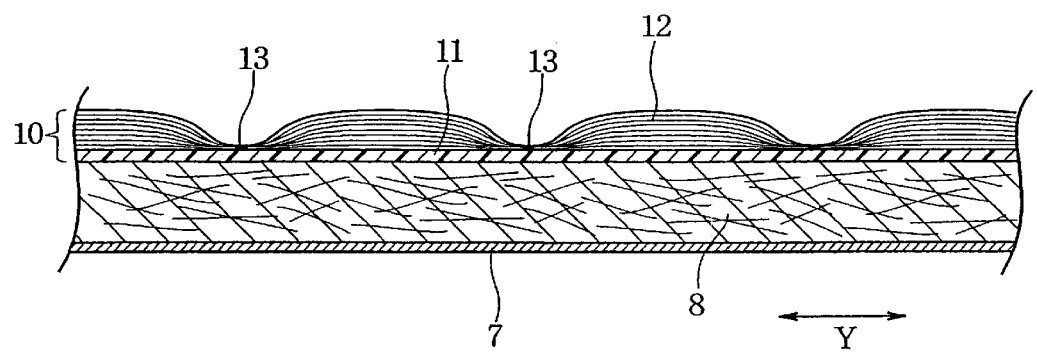
FIG. 3 is a partial section of the disposable diaper as viewed in the direction of arrow III of FIG. 2.
Figure 4A:
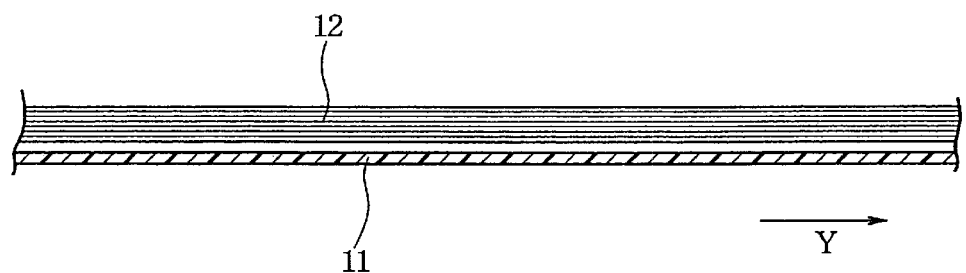
FIG. 4A is a partial section showing a condition where continuous filaments are stacked on a base sheet.
Figure 4B:
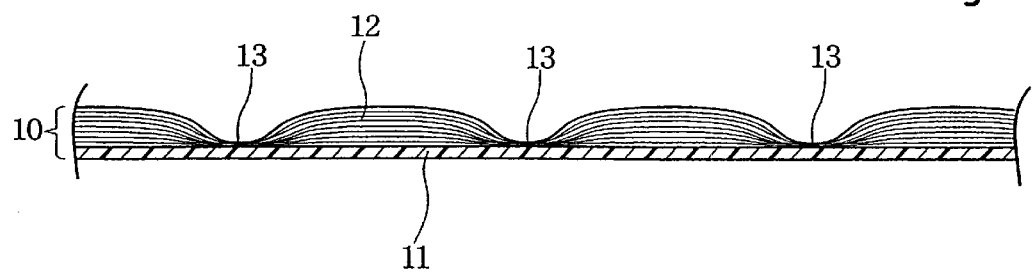
FIG. 4B is a partial section showing a condition where stacked base sheet and continuous filaments are partially fusion bonded for forming the backing sheet.
Figure 5:
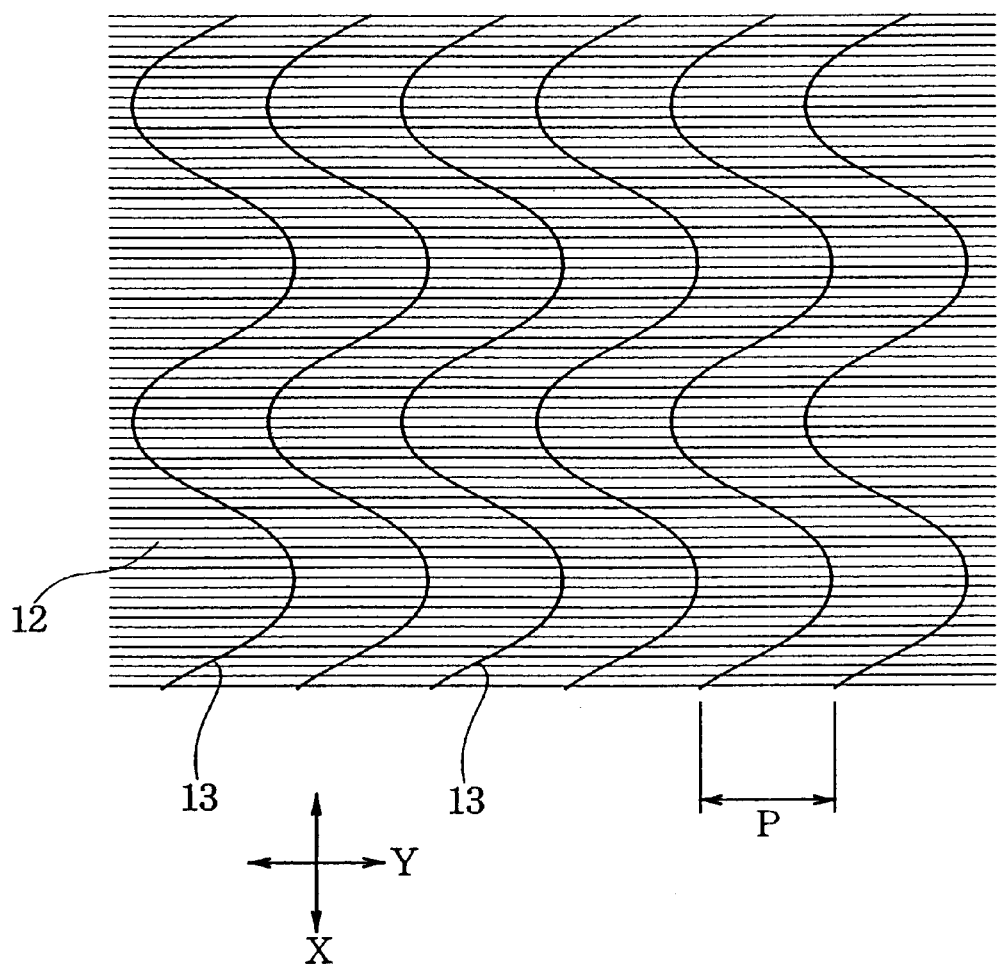
FIG. 5 is a partial plan view showing a fixing pattern of the base sheet and a continuous filament layer.

FIG. 1 is a perspective view showing a three-dimensional disposable diaper as an embodiment of an absorbent article according to the present invention; FIG. 2 is a developed plan view of the disposable diaper of FIG. 1 as viewed from outer surface; FIG. 3 is a partial section of the disposable diaper as viewed in the direction of arrow III of FIG. 2; FIG. 4A is a partial section showing a condition where continuous filaments are stacked on a base sheet; FIG. 4B is a partial section showing a condition where stacked base sheet and continuous filaments are partially fusion bonded for forming the backing sheet; and FIG. 5 is a partial plan view showing a fixing pattern of the base sheet and a continuous filament layer.

An absorbent article shown in FIGS. 1, 2 and 3 is a disposable diaper 1. In FIG. 2, a width direction (lateral direction) is defined as X direction and a longitudinal direction is defined as Y direction. The disposable diaper 1 has an intermediate portion 2, and a front portion 3 and a rear portion 4 at both ends of the intermediate portion 2, and is formed into an hourglass shape in plan view. When the disposable diaper 1 is worn on the wearer's body (not shown) in such a state as shown in FIG. 1, the intermediate portion 2 is fitted on a crotch portion, the front portion 3 is fitted on an abdominal portion, and the rear portion 4 is fitted on a hip portion. Flap portions 5a and 5a at laterally opposite sides of the rear portion 4 are fitted on the outer surface of the front portion 3. Then, engaging fasteners 6 and 6 secured on the flap portions 5a and 5a, respectively, are engaged on the outer surface of the front portion 3 for fitting the diaper on the wearer's body.

As shown in the section of FIG. 3, the disposable diaper 1 has a liquid permeable surface sheet 7 located on an inner side and a backing sheet 10 located on an outer side. Between the surface sheet 7 and the backing sheet 10, an absorbent core (absorbent layer) 8 is disposed.

The absorbent core 8 is in hourglass shape in plan view. The surface sheet 7 and the backing sheet 10 are bonded with each other in an outer periphery region beyond the outline of the absorbent core 8. In the intermediate portion 2, elastic yarns 9 and 9 are provided on left and right sides outside of the absorbent core 8. The elastic yarns 9 and 9 are fixed between the surface sheet 7 and the backing sheet 10. When the diaper is worn on the wearer's body, the surface sheet 7 and the backing sheet 10 are longitudinally contracted by the elastic yarns 9 and 9 to form so-called leg gather to wring down femoral region, as shown in FIG. 1.

The surface sheet 7 is liquid permeable and is formed of a liquid permeable non-woven fabric, a porous resin film formed with a large number of pores, or the like. The absorbent core 8 may be formed of a mixture of crushed pulp and SAP (superabsorbent polymer) wrapped with a liquid permeable paper, air laid pulp formed into a sheet through binder process, absorbing paper, non-woven fabric containing hydrophilic fibers as primary component, or the like.

As shown in FIG. 3, the backing sheet 10 is consisted of a liquid impermeable base sheet 11 and a filament layer 12 stacked on the outer side of the base sheet 11. The base sheet 11 is formed of a thermoplastic resin film, such as polyolefin type resin, in which fine pores or cuts are formed to provide moisture permeability (air permeability) and liquid blocking function. In the alternative, the base sheet 11 may be formed of a point bonded non-woven fabric or melt blown non-woven fabric of thermoplastic hydrophobic fibers, which is preferably subjected to a water repelling treatment. Here, the base sheet 11 is constructed to be heat-fusible.

The filament layer 12 is prepared by opening a filament bundle (called as "tow"), in which crimped continuous filaments are bundled. Individual continuous filaments forming the filament layer 12 extend in longitudinal direction (Y direction) of the disposable diaper 1 without interruption.

In this embodiment, as shown in FIG. 2, the entirety of the backing sheet 10 is formed of a laminate of the base sheet 11 and the filament layer 12. That is, the filament layer 12 is provided over the entire outer surface of the disposable diaper 1. However, it is also possible to provide the filament layer 12 on the base sheet 11 only at a center region except for the flap portions 5b and 5b on laterally opposite sides of the front portion 3 and the flap portions 5a and 5a on laterally opposite sides of the rear portion 4, so that at the flap portions 5a, 5a and 5b, 5b, the backing sheet 10 is formed only of the base sheet 11.

The continuous filaments forming the filament layer 12 are formed of hydrophobic synthetic resin which can be fusion bonded with the base sheet 11. For example, the continuous filaments may be conjugated synthetic fibers of core-sheath structure, such as those of PE/PET, PE/PP or the like, side-by-side type synthetic fibers, such as those of PE/PET, PE/PP or the like, or mono fibers, such as those of PE, PP, PET or the like. It is also preferred that the continuous filaments contain inorganic filler for whitening, such as titanium oxide or the like, in the content of 0.5 to 10% by weight. By whitening process, the surface of the backing sheet 10 may be provided external appearance similar to cloth.

On the other hand, when colored filaments are used as the continuous filaments, the outer surface of the disposable diaper 1 can be colored to provide superior external appearance. For example, when the continuous filaments are conjugated synthetic fibers of core-sheath structure, the resin of the core portion is colored into red, blue, violet, green or the like, and the resin of the sheath portion is transparent, semi-transparent or translucent. The filament layer 12 using such continuous filaments provides external appearance having luster and slightly lowered chrominance of the color to exhibit light color on the outer surface of the diaper for better appearance.

In case of the side-by-side type conjugated fibers, it is possible to color only one resin forming one side portion. In case of the mono fibers, it is possible to color the entire mono fibers. The individual continuous filaments may have a circular or modified cross-section.

Crimping is provided for the continuous filaments upon production by means of crimper and number of crimp is increased by pre-heating calender or hot air treatment. In the alternative, through pre-heating calender, drawing and relaxing are repeated to cause strain in orientation of resin forming the continuous filaments to cause crimp in coil form.

Opening of a bundle of crimped continuous filaments can be performed as following. While the bundle is transported between transporting rolls, tension force is applied in the direction along which the filaments extend, and then the tension force is released. These processes are repeated to separate individual continuous filaments from each other for opening. In the alternative, it is also possible to perform opening of the bundle by urging sliding plates onto the bundle from opposite sides. In this method, the bundle transported between transporting rolls is slidingly contacted with the sliding plates, and individual filaments are separated from each other by sliding contact force for opening. The latter method employing the sliding plates has been disclosed in commonly owned co-pending U.S. patent application Ser. No. 09/935,407 for "METHOD AND APPARATUS FOR OPENING CONTINUOUS FILAMENTS" (claiming priority based on Japanese Patent Application No. 2000-265458). The disclosure of the above-identified commonly owned co-pending U.S. Patent Application is herein incorporated by reference. The bundle of continuous filaments thus opened has a small filament density and a large apparent width.

Furthermore, the opened filament bundle is spread (widened) in the width direction to have a uniform bulkiness and to have a width substantially matching with or larger than the width of the disposable diaper 1.

The manufacturing method of the backing sheet 10 is as illustrated in FIG. 4A. The base sheet 11 is transported through transporting rolls. The filament layer 12 of the opened and spread continuous filaments is transported in the same direction as transporting direction of the base sheet 11. Thus, the filament layer 12 is stacked on the base sheet 11. The filament layer 12 and the base sheet 11 thus stacked are clamped by welding rolls, at least one of which contains a pattern of protrusions for embossing on the peripheral surface, for forming fixing lines 13. At respective fixing lines 13, the continuous filaments of the filament layer 12 and the base sheet 11 are heat fused or welded by induction heating with ultrasonic wave to thereby form into a sheet.

As shown in FIGS. 1, 2 and 5, the individual fixing lines 13 extend across the backing sheet 10 in the X direction in the form of continuous line approximated to trigonometric curve. In the Y direction along which the individual continuous filaments extend, the fixing lines 13 are spaced apart from each other by a given pitch P. The pitch P of the fixing lines 13 is in a range of 10 to 60 mm. By forming the fixing lines 13 with the pitch P within the range set forth above, soft feeling of the stacked body of the base sheet 11 and the filament layer 12 may not be degraded.

However, fixing lines should not be limited to the shown wavy shape but may extend in various forms, for example, in the form of straight line or V-shaped line. It is also possible to provide a plurality of short fixing lines intermittently arranged at a given interval in the X direction, so long as consideration is given to prevention of falling out of filaments. Various alternation of the short fixing line patterns are disclosed in commonly owned co-pending U.S. patent application Ser. No. 09/939,222, for "ABSORBENT ARTICLE EMPLOYING SURFACE LAYER WITH CONTINUOUS FILAMENT AND MANUFACTURING PROCESS THEREOF" (claiming priority based on Japanese Patent Application No. 2000-265467). The disclosure of the above-identified commonly owned co-pending U.S. patent application will be herein incorporated by reference. Of course, it is possible to replace the short fixing lines with circular dot-shaped fixing portions or the like.

The filament layer 12 has a basis weight in a range of 5 to 100 g/m$^2$, and preferably in a range of 10 to 60 g/m$^2$. A thickness of the filament layer 12 in the portion where the fixing line 13 is not formed, is preferably greater than or equal to 0.5 mm. Fineness of the continuous filaments is in a range of 1.1 to 20 dtex, and preferably in a range of 1.1 to 11 dtex.

In the individual continuous filaments, number of crimp is in a range of 5 to 30 per inch, and preferably in a range of 15 to 30, and crimp modulus of elasticity is preferably greater than or equal to 70%.

Number of crimp is based on JIS L-1015 and crimp modulus of elasticity is based on JIS L-1074. In case of the filament of a fineness less than 5.5 dtex, an initial load of 0.49 mN is applied in pulling direction, and in case of the filament of a fineness greater than or equal to 5.5 dtex, an initial load of 0.98 mN is applied in pulling direction. Number of crimp referred to is number of threads (peaks) per 1 inch (25 mm) when the initial load is applied.

On the other hand, the crimp modulus of elasticity is expressed by:

$$\{(b-c)/(b-a)\} \times 100 (\%)$$

wherein a is a length of filament when the initial load is applied, b is a length when the crimp is stretched by applying a tension force of 4.9 mN per 1.1 dtex for 30 seconds, and c is a length as applied the initial load again after 2 minutes from releasing the tension force.

The filament layer 12 may also be formed of split yarns. Split yarns are prepared by splitting a film in a width direction to form filaments joined in net form.

In the disposable diaper 1 thus far described, the filament layer 12 formed of the longitudinally extending continuous filaments is provided on the surface of the backing sheet 10, which appears on the outer surface of the diaper in a worn (three-dimensional) state as shown in FIG. 1. Since all the filaments extend in the longitudinal direction in the filament layer 12, the surface thereof is quite smooth (particularly in the longitudinal direction), as compared with an ordinary non-woven fabric in which fibers extend in many directions. Moreover, since the filament layer 12 is formed of the continuous filaments, no fiber end appears on the surface thereof. Therefore, the surface provides a pleasant feel to the touch.

On the other hand, since the base sheet 11 and the filament layer 12 are fixed only at the fixing lines 13, excessive stiff feeling due to fixing portions can be prevented. As shown in FIG. 1, upon worn on the wearer's body, the disposable diaper 1 is curved in the longitudinal direction. Here, since the fixing lines 13 extend in the X direction intersecting (perpendicularly intersecting) the curving direction, and the curving direction matches the direction along which the continuous filaments extend, resistance against bending as curved in the three-dimensional shape is small. Therefore, the diaper can softly conform to the wearer's body.

On the other hand, since the filament layer 12 is not subjected to pressurizing force in the region other than fixing lines 13, the filament layer 12 has high bulkiness to have high cushioning ability upon contacting.

In the worn condition shown in FIG. 1, the flap portions 5a and 5a on laterally opposite sides of the rear portion 4 are laid over the outer surface of the filament layer 12 of the front portion 3, then the engaging fasteners 6 and 6 fixed on the flap portions 5a and 5a are engaged on the outer surface of the filament layer 12.

Each engaging fastener 6 has a large number of engaging projections of a hook shape, mushroom shape or the like, on the surface to confront the filament layer 12. In the filament layer 12, individual continuous filaments have freedom of movement between adjacent fixing lines 13. Therefore, when the engaging fastener 6 is pushed thereto, head portions of the engaging projections easily penetrate between the continuous filaments. Thus, the head portions of the engaging projections are certainly engaged to the continuous filaments.

Therefore, it becomes unnecessary to provide an engagement receptacle sheet (i.e., a sheet having a number of loops or the like engageable with the head portions of the engaging protrusions) on the outer surface of the front portion 3. In the diaper 1, the engaging fastener 6 can be certainly engaged without such an engagement receptacle sheet. Moreover, the engaging fastener 6 demonstrates engaging force for any portion of the filament layer 12. Therefore, when the disposable diaper 1 is worn to conform to the body shape of the wearer, the engaging fastener can be engaged at arbitrary position.

Figure 6:
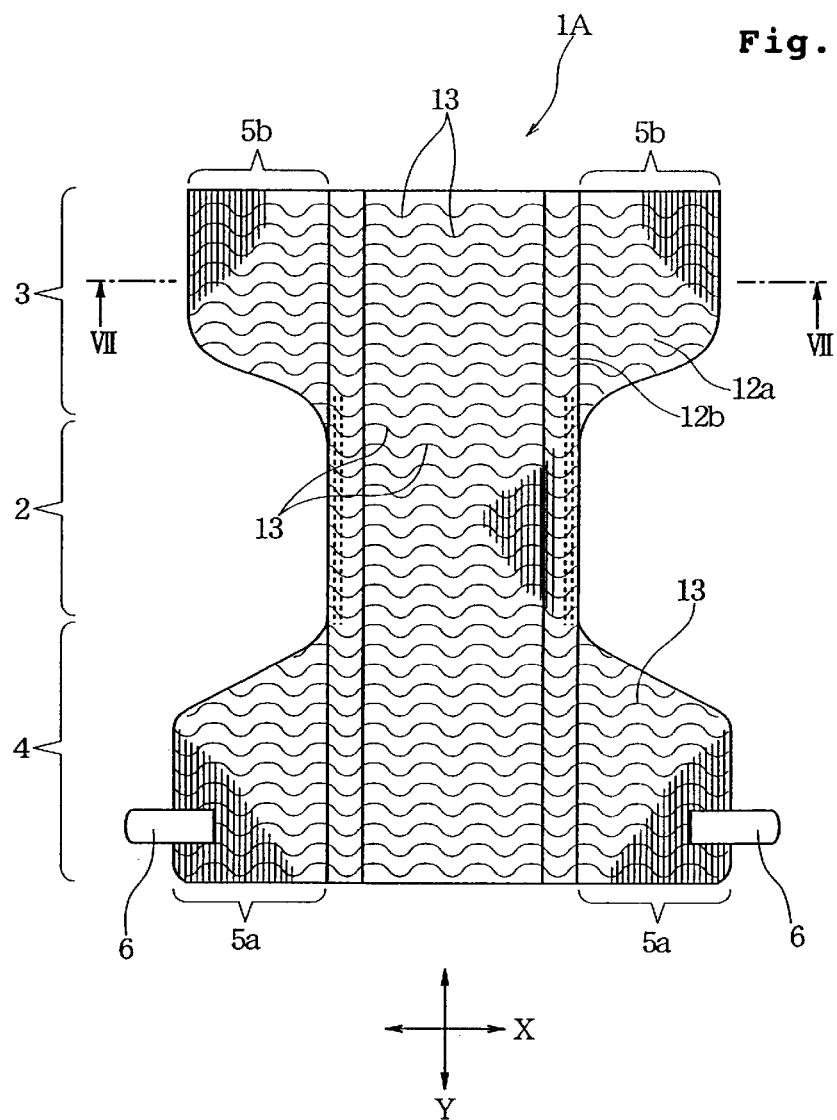
FIG. 6 is a developed plan view of a disposable diaper as another embodiment of an absorbent article according to the present invention.
Figure 7:
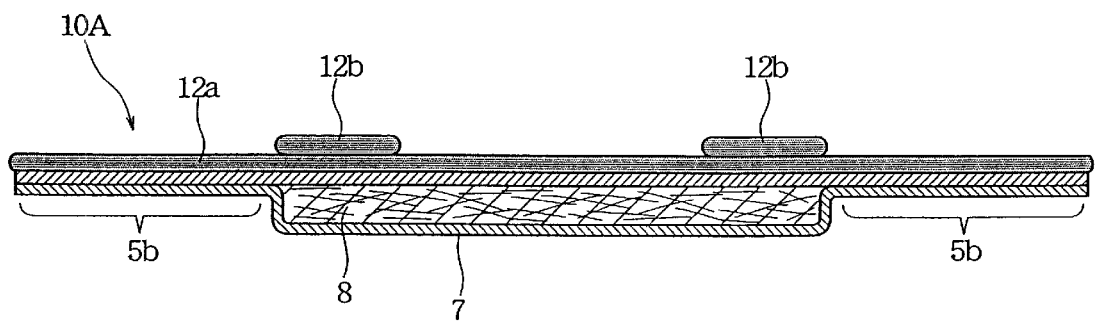
FIG. 7 is a section taken along line VII—VII of FIG. 6.

FIG. 6 is a developed plan view of a disposable diaper 1A as another embodiment of an absorbent article according to the present invention, and FIG. 7 is a section taken along line VII—VII of FIG. 6.

In the shown embodiment, a backing sheet 10A is formed by stacking a first filament layer 12a on the outer surface of the base sheet 11, and further stacking a second filament layer 12b. The base sheet 11, the first filament layer 12a and the second filament layer 12b are fused and fixed together by wave form fixing lines 13.

While the first filament layer 12a is provided over substantially entire area of the disposable diaper 1A, the second filament layer 12b is provided in the form of two parallel strips (bands) extending in the longitudinal direction inwardly of the flap portions 5a, 5a and 5b, 5b. Both the first filament layer 12a and the second filament layer 12b (i.e., two strips) are formed of continuous filaments extending in the longitudinal direction (Y direction) without interruption.

In the regions where the two strips of the second filament layer 12b are provided, basis weight of the continuous filaments becomes large and bulkiness also becomes large. Therefore, upon worn on the wearer's body, engaging strength of the engaging fasteners 6 and 6 can be increased by engaging the engaging fasteners 6 and 6 to the regions having the two strips of the second filament layer 12b, to more certainly prevent displacement of the diaper as worn.

Although the present invention has been illustrated and described with respect to exemplary embodiment thereof, it should be understood by those skilled in the art that the foregoing and various other changes, omission and additions may be made therein and thereto, without departing from the spirit and scope of the present invention. Therefore, the present invention should not be understood as limited to the specific embodiment set out above but to include all possible embodiments which can be embodied within a scope encompassed and equivalent thereof with respect to the feature set out in the appended claims.

For instance, the absorbent article of the present invention should not be limited to the disposable diaper, and is also applicable for incontinence pad (urine-absorbing pad), sanitary napkin, panti-liner and so forth.

As set forth above, in the present invention, since the layer of the continuous filaments extending in the longitudinal direction is used in the backing sheet of the absorbent article, the outer surface is soft enough to provide satisfactory cushioning ability. Also, the overall diaper can be made soft. Furthermore, the engaging fastener can be engaged with the continuous filament layer. Moreover, the backing sheet having the base sheet and the filament layer fixed together can be easily manufactured.

What is claimed is:

1. An absorbent article comprising:

a liquid permeable surface sheet;

a backing sheet;

an absorbent layer located between said surface sheet and said backing sheet;

said backing sheet including a liquid impermeable base sheet and a layer of continuous filaments individually extending an entire length of the base sheet along a longitudinal direction of the absorbent article and stacked on an outer surface of said base sheet, and said base sheet and said continuous filament layer being partially fixed to each other.

2. The absorbent article as set forth in claim 1, wherein said base sheet and said continuous filament layer are fixed with each other at a plurality of fixing lines extending in a direction traversing said continuous filaments and spaced apart in a direction along which said continuous filaments extend.

3. The absorbent article as set forth in claim 2, wherein said fixing line is in wave shaped pattern.

4. The absorbent article as set forth in claim 1, wherein said absorbent article has an intermediate portion for confronting a crotch portion of a wearer, a front portion for confronting an abdominal portion of a wearer and a rear portion for confronting a hip portion of a wearer, and said rear portion is provided on laterally opposite side portions thereof with fasteners having engaging projections for engaging with said continuous filament layer in said front portion.

5. The absorbent article as set forth in claim 4, wherein bulkiness of said continuous filament layer is increased at a region to which said fastener is intended to be engaged.

6. The absorbent article as set forth in claim 1, wherein said continuous filaments are colored.

* * * * *